United States Patent
Falkenstein et al.

[11] Patent Number: 5,928,225
[45] Date of Patent: Jul. 27, 1999

[54] DEVICE FOR THE TREATMENT OF BENIGN PROSTATIC HYPERPLASIA

[76] Inventors: Werner Falkenstein, Am Hochwald 26, D-82319; Rolf Muschter, Waxensteinstrasse 36, D-82319, both of Starnberg, Germany

[21] Appl. No.: 08/809,099
[22] PCT Filed: Sep. 19, 1995
[86] PCT No.: PCT/EP95/03696
  § 371 Date: Jun. 20, 1997
  § 102(e) Date: Jun. 20, 1997
[87] PCT Pub. No.: WO96/09010
  PCT Pub. Date: Mar. 28, 1996

[30] Foreign Application Priority Data

Sep. 19, 1994 [DE] Germany .............. 44 33 352

[51] Int. Cl.$^6$ ............................................... A61B 17/38
[52] U.S. Cl. ................................................. 606/28; 606/29
[58] Field of Search ........................ 606/28, 29, 30, 606/31, 27

[56] References Cited

U.S. PATENT DOCUMENTS 4,672,962  6/1987  Hershenson .................. 606/28

FOREIGN PATENT DOCUMENTS 3315303  11/1984  Germany .
3518245  11/1986  Germany ............................. 606/29
2138297  10/1984  United Kingdom ................... 606/31
2269538   2/1994  United Kingdom .
9510253   4/1995  WIPO .

Primary Examiner—Michael Buiz
Assistant Examiner—Julian W. Woo
Attorney, Agent, or Firm—Ostrolenk, Faber, Gerb & Soffen, LLP

[57] ABSTRACT

A device for treating benign prostatic hyperplasia by heat treatment has an elongated contact applicator (10) with a heating tip at its free end (18), the tip being insulated by thermal insulation from the rest of the contact applicator, and a control device for feeding electric power to the contact applicator (10) is provided in such a manner that the heat given off by the jacketed heating conductor is restricted to a heating region (15) adjacent to the free end (18) of the contact applicator. The control device (20) comprises a control unit for controlling the feeding of electric power in accordance with a preset program. The heating region (15) can be brought into direct or indirect contact with the tissue area (2, 3, 4) to be treated.

13 Claims, 3 Drawing Sheets

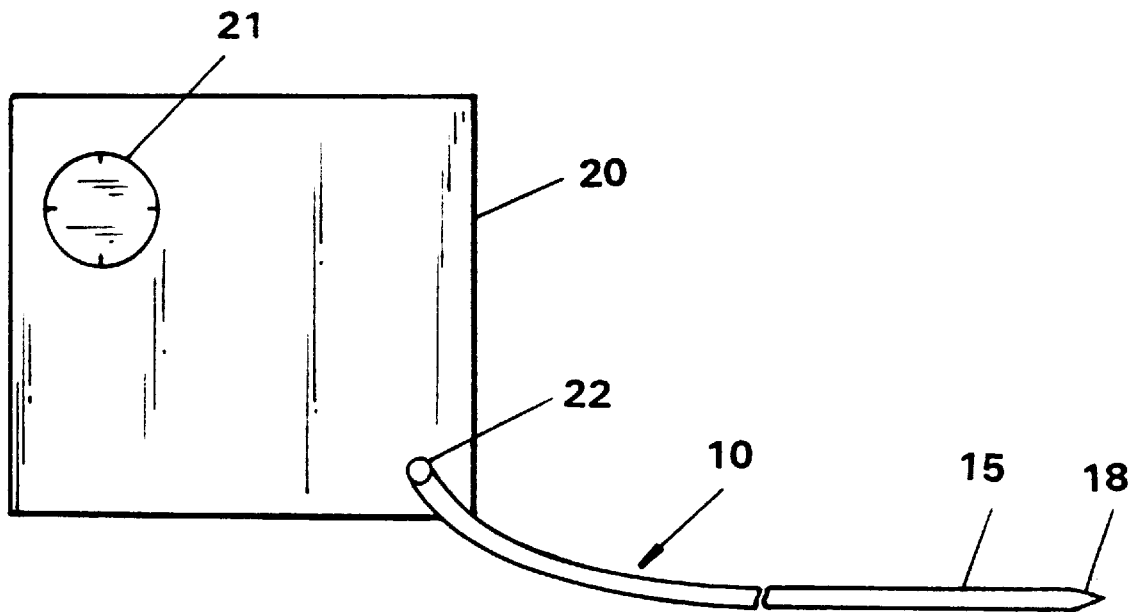
FIG. 1
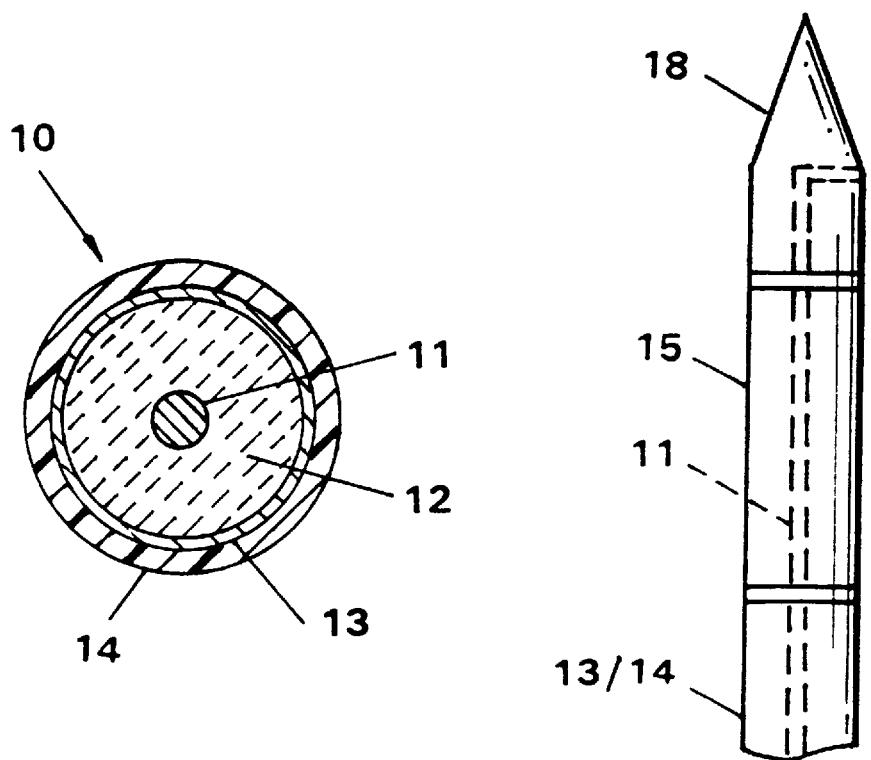
FIG. 2
FIG. 3

DEVICE FOR THE TREATMENT OF BENIGN PROSTATIC HYPERPLASIA

BACKGROUND OF THE INVENTION

The present invention relates of a device for the treatment of benign prostatic hyperplasia (BPH), which is a benign proliferation of the prostate gland which can, and frequently does, lead to an obstruction or constriction of the urethra which extends through the prostate and thus to considerable impairment of urination and emptying of the bladder.

For the treatment of BPH, cold (cryosurgery, now abandoned) and heat, produced, for instance, by microwaves or ultrasonics have been used for a long time, in addition to surgical methods in order to obliterate the obstructing tissue.

In recent years, laser applications have been increasingly proposed in which the obstructing tissue is heated and denatured, or even directly vaporized, either in contact with the tissue or without contact by radiation with laser light. The laser application can be effected both from outside the tissue and from within the tissue (interstitial).

It is common to all these methods that the treatment devices are very large and expensive, both to purchase and to use. It has furthermore been attempted to destroy prostatic tissue by means of metal wires or metal plates arranged on the end of special instruments, which are introduced into the urethra and made red hot by electric current, which are in contact with the prostatic tissue. The considerable side effects due to poor control of the effects have, however, prevented this method from becoming a generally accepted method of operation. A survey of the present state of knowledge with regard to the effects of cold, heat and light on prostatic tissue, as well as the present state of medical technology can be noted from an article by R. Muschter and A. Hofstetter entitled "Thermische Therapie der benignen Prostata- hyperplasie" [Thermal therapy of benign prostatic hyperplasia], Münchener Medizinische Wochenschrift 134 (40):630–634, 1992.

In an article by A. Roggan and G. Müller, "Computer simulations for the irradiation planning of LITT", MEDTECH 4(2):18–24, 1993, computer simulations which describe the action of lasers in the near infrared are indicated. Due to the great depth of penetration of these wavelengths, the large coagulation regions of diameters of 25 to 30 mm which have been experimentally described upon interstitial application have been verified and explained on the phantom.

The use of a pure heat source was considered insufficiently gradated as compared with this, since the effect of the heat conduction which is applied in this connection, due among other things to the cooling action of the blood flowing through the tissue, limits the necrosis From Federal Republic of Germany 33 15 303, a method and a device are known for producing defined thermal damage to biological tissue in which, however, only a superficial coagulation is desired and not a depthwise action. In that known device, a heating element is provided by a coaxial construction consisting of a well-conducting center conductor and a tubular outside section consisting of a material having electrical resistance which forms a heating region. The tubular heating element is of relatively low resistance and is acted on by very short current pulses of high amplitude. Furthermore, said heating element has dimensions which do not permit insertion into the interior of tissue.

The heating tip can be fed both with alternating current, particularly an alternating current of higher frequency, and with direct current.

Due to the fact that the heating tip itself or the heating region is thermally insulated from the rest of the contact applicator, a targeted application of the heat can be obtained without neighboring regions of tissue being damaged.

In the device of the invention, electric current is used as source of heat for the interstitial thermal therapy, in which connection the side effects which occur with the previously known devices being dependably avoided in a simple manner.

DESCRIPTION OF THE INVENTION

By the electrically heated contact applicator of the device of the invention both interstitial coagulation and transurethral coagulation and vaporization are possible, there being obtained coagulation of the tissue above about 60° C. and carbonization, and finally vaporization, above about 100° C.

Although reference has been had above in particular to the thermal destruction of tissues by interstitial or surface application of heat by electrically heated elements in the region of the prostate, this possibility of use is not limited to this, but is possible in every organ system.

The heating tip can be fed both with alternating current, particularly an alternating current of higher frequency, and with direct current.

BRIEF DESCRIPTION OF THE DRAWINGS

The invention will be explained in further detail below with reference to embodiments shown in the drawing, in which:

FIG. 1 is a diagram of an embodiment of the device;

FIG. 2 is a cross section through a part of the contact applicator of the device of FIG. 1;

FIG. 3 is a more detailed view of the front end of the contact applicator of t he device of FIG. 1;

DETAILED DESCRIPTION OF THE DRAWINGS

Figure 4:
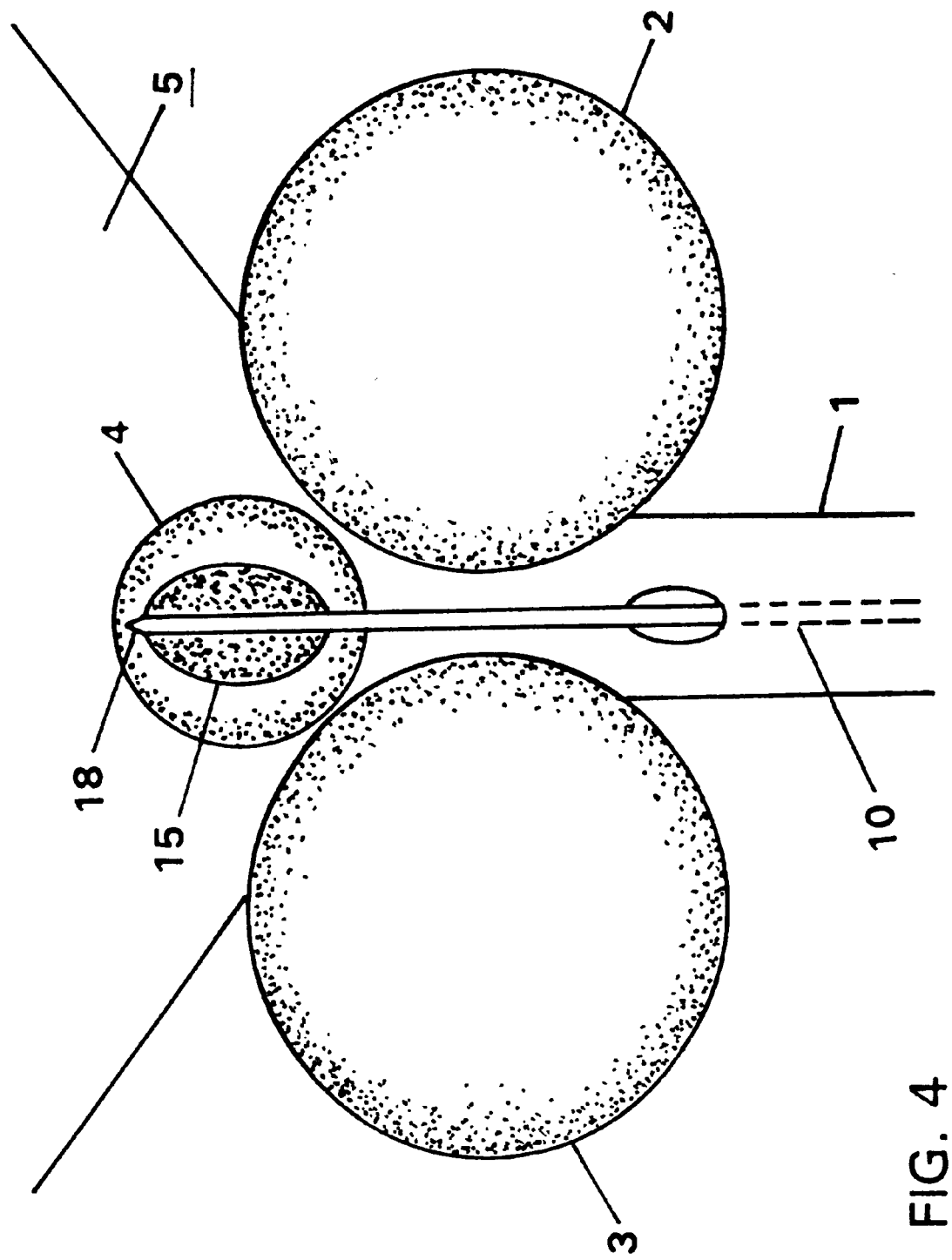
FIG. 4 is a diagrammatic showing of the use of the device.

FIG. 1 shows diagrammatically an embodiment of the device which comprises a contact applicator 10 and a control device 20.

In the embodiment shown, the contact applicator is formed by a jacketed heating conductor, i.e. a central conduct or 11 (FIG. 2) which is embedded in a preferably ceramic insulating material 12 which is a very good conductor of heat and is surrounded coaxially by a metal jacket 13, in which connection the outside diameter of the metal jacket 13 can be very slight, for instance being on the order of magnitude of between 0.3 and 3 mm.

The central conductor 11 is formed by a resistance wire over a very small region 15 of the length of the contact applicator 10, while the rest of the metal conductor is formed by copper material which is a good conductor of electricity so that the production of heat is limited solely to the heating region 15 of the heating conductor section and thus can be defined very precisely.

Instead of the jacketed heating conductor there can also be used a heating tip in which the heating region 15 is separated from the other parts of the contact applicator by a heat insulation, so that only this heating region 15 is heated.

As can be noted from FIG. 3, this contact applicator can have a needle tip 18, which permits introduction into the tissue to be treated, and is adjacent to this tip 18, at a predetermined distance away, there is arranged the heating region 15 of the jacketed heating conductor. In this connection, both the tip 18 and the following region of the contact applicator in the direction towards the device 10 remains cool, so that a very precise control of the feed of heat to given regions of tissue can be obtained. However, the jacketed heating conductor may also be so thin or rounded at its end that a separate tip is not necessary and thus the end of the contact applicator directly forms the heating region.

For use in BPH, the heating region 15 which produces the heat has, for instance, a length of between 20 and 40 mm.

The jacket 13 of the contact applicator can be coated with a plastic material 14, such as polytetrafluorethylene or another material which is sufficiently heat resistant and prevents adherence to the tissue, particularly after the denaturing of the latter, or at least prevents it to such an extent that the contact applicator 10 which has been introduced into the tissue can be removed again without any major tearing of tissue.

Due to the small diameter of the jacketed heating conductor, sufficient flexibility remains, but there is a sufficiently large surface for the transmission of the heat to the tissue without the danger of carbonizing the tissue. This diameter is preferably within the range of 1 to 3 mm.

The control device 20 is preferably so developed that, at the start of the treatment, a high electric power is fed to the heating region 15 of the jacketed heating conductor, leading to the shortest possible heating-up phase of the tissue to be denatured.

The electric power can be fed in the from of an alternating current, particularly an alternating current of higher frequency, or as a direct current.

During the actual therapy phase, the feeding of power to the jacketed heating conductor can then be reduced so that the tissue is denatured without carbonization or vaporization effects occurring.

Typical values of temperature in the tissue for the denaturing are within the range of between 60° C. and 100° C.

The control device 20 can have a corresponding control unit which permits the feeding of energy to the jacketed heating conductor in accordance with a preset program, in which connection individual programs can be selected by a switch 21.

A typical heating phase can, for instance, be as follows:

10 seconds: heating power 10 watts;

20 seconds: heating power 7.5 watts;

2.5 minutes: heating power 5 watts.

In this connection, the electric power fed to the jacketed heating conductor is preferably controlled by sensors which are either introduced separately into the tissue or are located on the tip 18 or in the heating region 15 of the jacketed heating conductor itself.

In this connection temperature sensors are preferably used, but other sensors can also be used which make it possible to recognize and monitor the effect of the denaturing, such as, for instance, conductivity sensors, resistance sensors, gas sensors, optical sensors, which can detect properties of the tissue which change during the treatment.

Figure 5:
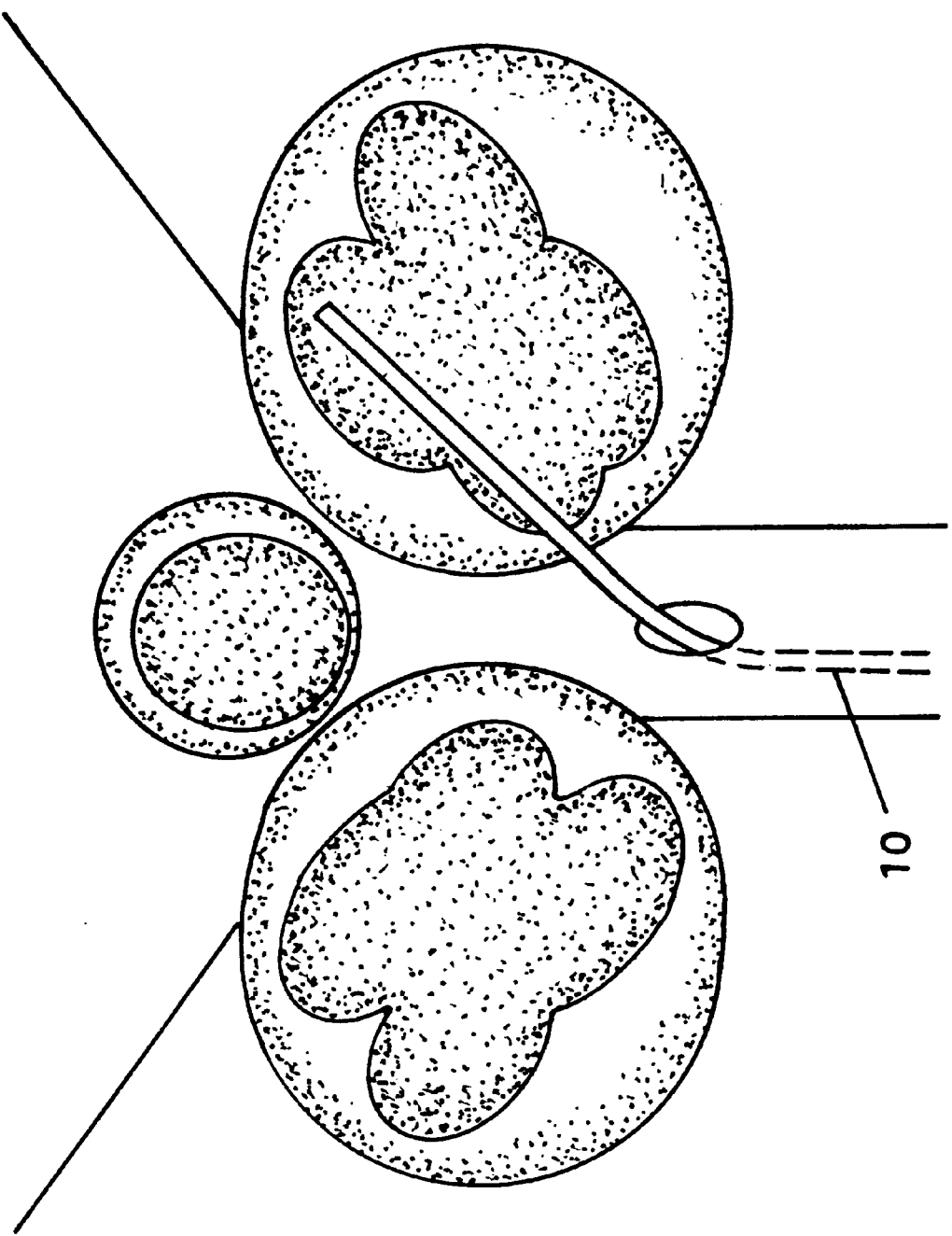
FIG. 5 is a diagrammatic showing of another use of the device.

FIGS. 4 and 5 show examples of the use of the contact applicator for the treatment of BPH. In these drawings, 2 and 3 are the left and right lateral lobes of the prostate, while 4 is the middle lobe of the prostate and 5 is the bladder. The contact applicator can be introduced through the urethra or by some other route, for instance from the perineum through the skin into the tissue of one or more prostate lobes 2 to 4 by means of the tip, the arrangement being such that the heating region 15 comes into contact with the region of the tissue to be treated.

We claim:

1. A device for treating benign prostatic hyperplasia by heat treatment which comprises an elongated contact applicator (10) having a tip (18) at its free end which permits the introduction of the contact applicator into the tissue to be treated and which is arranged at a predetermined distance from a heating region (15) which is insulated by heat insulation from the rest of the contact applicator in the manner that the heat given off is limited to the heating region adjacent to the free end of the contact applicator; a control device for feeding electric power to the contact applicator (10), the control device (20) comprising a control unit for controlling the electric power feed in accordance with a preset program; and wherein the heating region (15) has a diameter within the range of 1 to 3 mm and can be brought into direct or indirect contact with the region (2, 3, 4) of the tissue to be treated.

2. A device according to claim 1, wherein the elongated contact applicator (10) is a jacketed heating conductor (11–14) with locally very strongly delimited delivery of heat.

3. A device according to claim 2, wherein the jacketed heating conductor (11–14) has a central conductor (11) which is embedded in an insulating material (12) which is a very good conductor of heat and is surrounded coaxially by a metal jacket (13); and that the central conductor (11) is formed by a resistance wire only over the heating region (15) while the rest of the central conductor is formed of material which is a good conductor of electric current.

4. A device according to claim 1, wherein the length of the heating region (15) of the heating tip is between 10 and 40 mm.

5. A device according to claim 1, wherein at least the heating region (15) of the contact applicator (10) is coated with or surrounded by a heat-resistant material (14) which reduces the adherence to tissue.

6. A device according to claim 1, wherein the control device (21) preset program in succession first delivers a high electric power for a short time and then a reduced electric power for a longer time to the contact applicator (10).

7. A device according to claim 6, wherein the short time during which a high electric power is fed is about 10 seconds, while the reduced electric power is fed over a period of about 20 seconds.

8. A device according to claim 1, characterized by the fact that the power fed to the heating region (15) is measured by sensors and used for the control.

9. A device according to claim 1, characterized by the fact that the tip of the contact applicator has sensors for detecting the properties of the tissue treated.

10. A device according to claim 1, characterized by the fact that the heating tip is fed with an alternating current of high frequency.

11. A device according to claim 1, characterized by the fact that the heating tip is fed with direct current.

12. A device according to claim 3, in which the insulating material is a ceramic.

13. A device according to claim 12, wherein the length of the heating region (15) of the heating tip is between 10 and 40 mm and wherein the control device (21) preset program in succession first delivers a high electric power for a short time and then a reduced electric power for a longer time to the contact applicator (10).

* * * * *